United States Patent [19]

Satake

[11] Patent Number: 4,800,280
[45] Date of Patent: * Jan. 24, 1989

[54] MEASURING APPARATUS FOR AMYLOSE AND/OR AMYLOPECTIN CONTENT IN RICE

[75] Inventor: Toshihiko Satake, Higashihiroshima, Japan

[73] Assignee: 501 Satake Engineering Co., Ltd., Tokyo, Japan

[*] Notice: The portion of the term of this patent subsequent to Jun. 21, 2005 has been disclaimed.

[21] Appl. No.: 97,748

[22] Filed: Sep. 17, 1987

[30] Foreign Application Priority Data

Sep. 19, 1986 [JP] Japan .............................. 61-222493
Dec. 27, 1986 [JP] Japan .............................. 61-315799

[51] Int. Cl.$^4$ ............................................. G01J 1/00
[52] U.S. Cl. .................................................. 250/339
[58] Field of Search ..................... 356/445, 448, 446; 250/339, 358.1, 341, 359.1; 73/866

[56] References Cited

U.S. PATENT DOCUMENTS 4,040,750  8/1977  Zwiener .............................. 356/448
4,253,766  3/1981  Funk .................................. 356/446
4,400,086  8/1983  Webster .............................. 250/576
4,404,642  9/1983  Rosenthal ........................... 250/339
4,692,620  9/1987  Rosenthal ........................... 250/339

FOREIGN PATENT DOCUMENTS 0125664 10/1981  Japan ................................. 356/445

Primary Examiner—Stewart J. Levy
Assistant Examiner—Robert R. Raevis
Attorney, Agent, or Firm—Wegner & Bretschneider

[57] ABSTRACT

An apparatus for measuring amylose and/or amylopectin content in rice. A near infrared light beam having its wavelength in a range of from about 1900 nm to about 2500 nm is applied to sample rice (5). A detector (26, 27,28) receives light reflected from and/or transmitted through the sample rice (5), to generate signals representative of luminous intensity of the received light. A memory device (122) has stored therein content conversion coefficients set for the amylose and/or amylopectin. A calculation device (123) calculates the amylose and/or amylopectin content in the sample rice (5), based on the detecting signals from the detector (26,27,28) and the content conversion coefficients stored in the memory device (122). The calculated content is displayed by a display device (126,127).

18 Claims, 8 Drawing Sheets

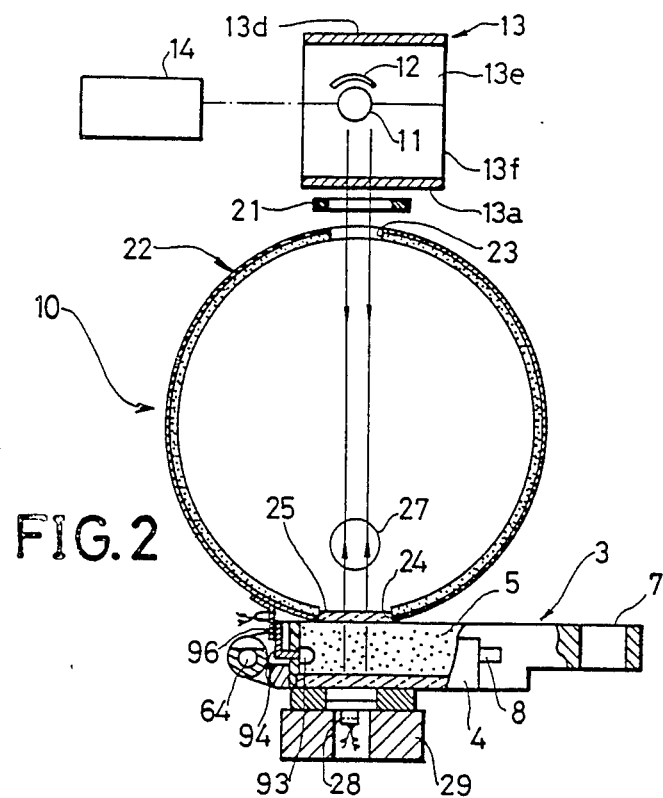
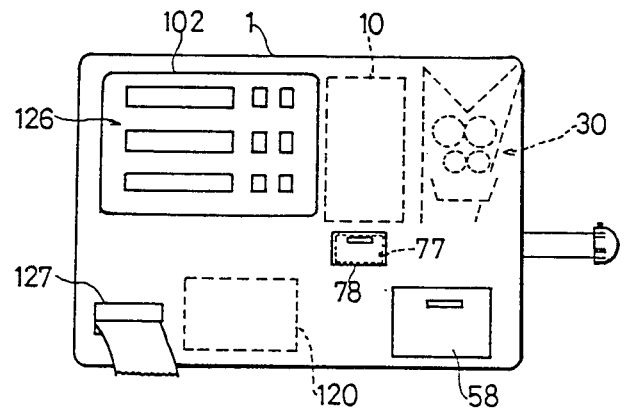

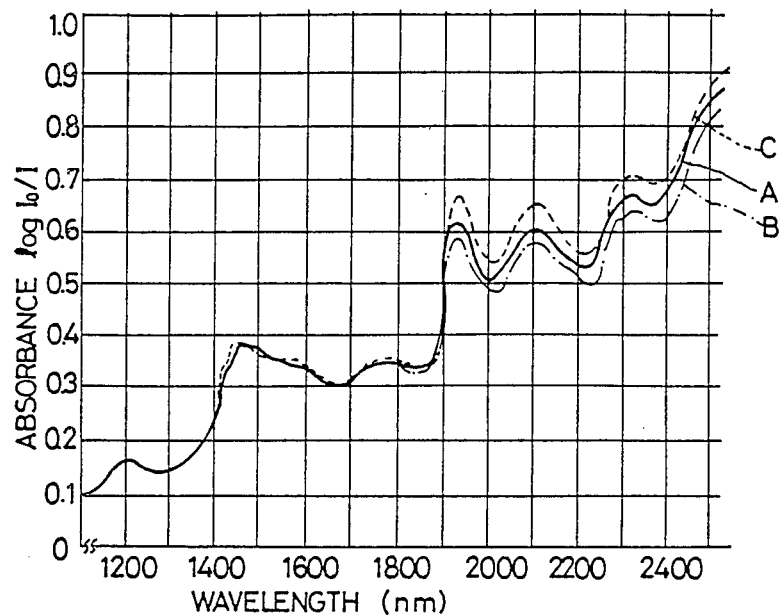
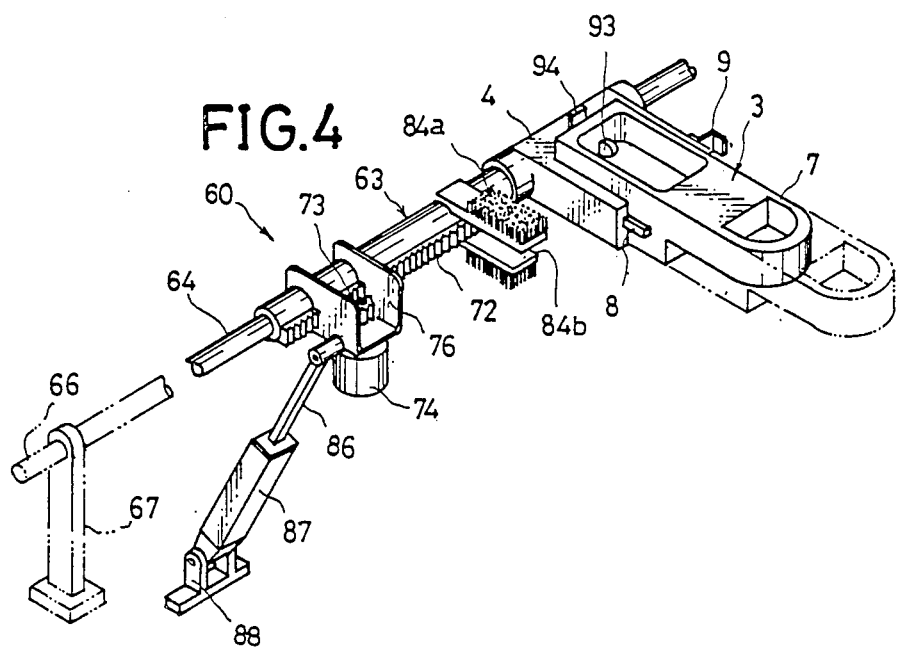

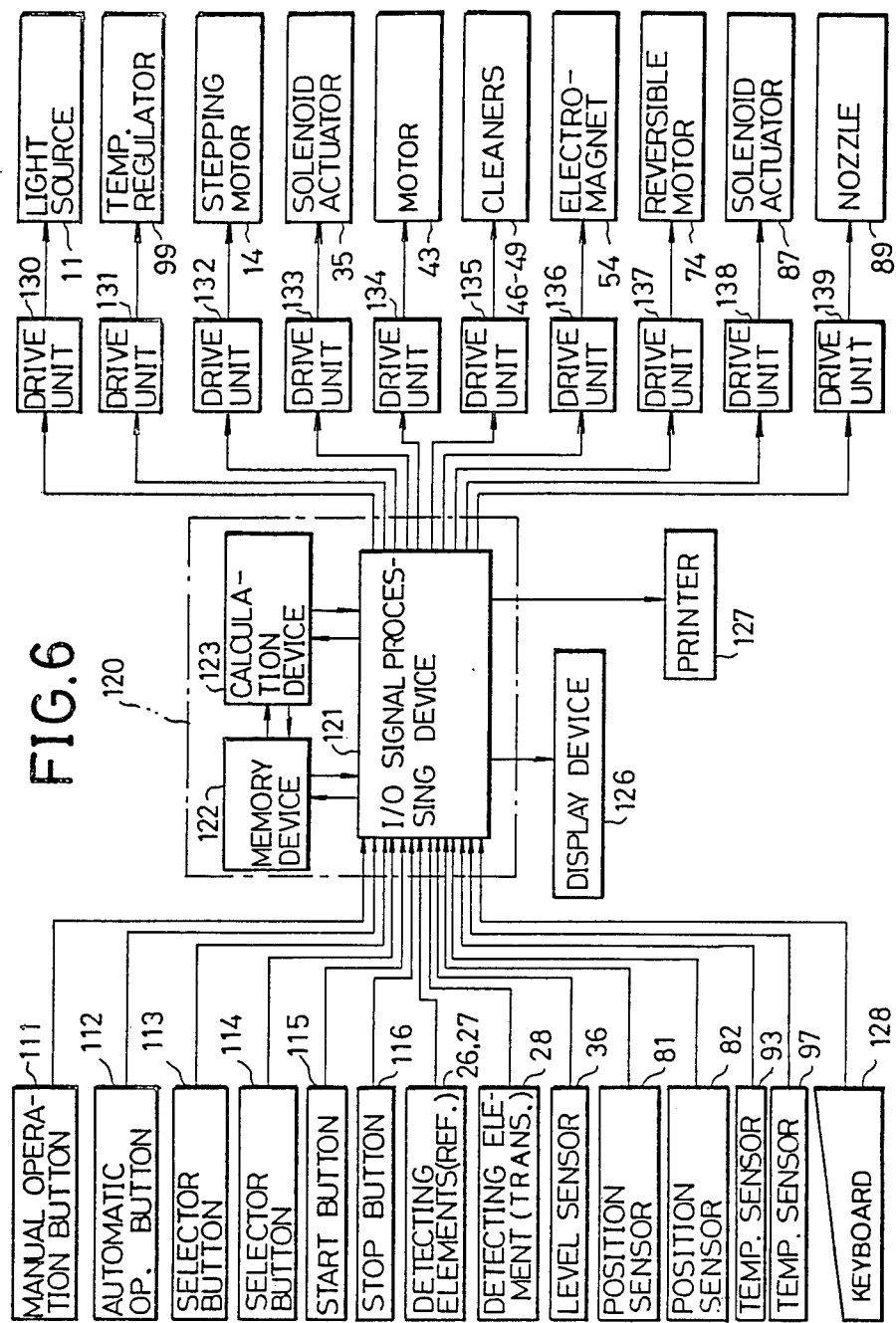

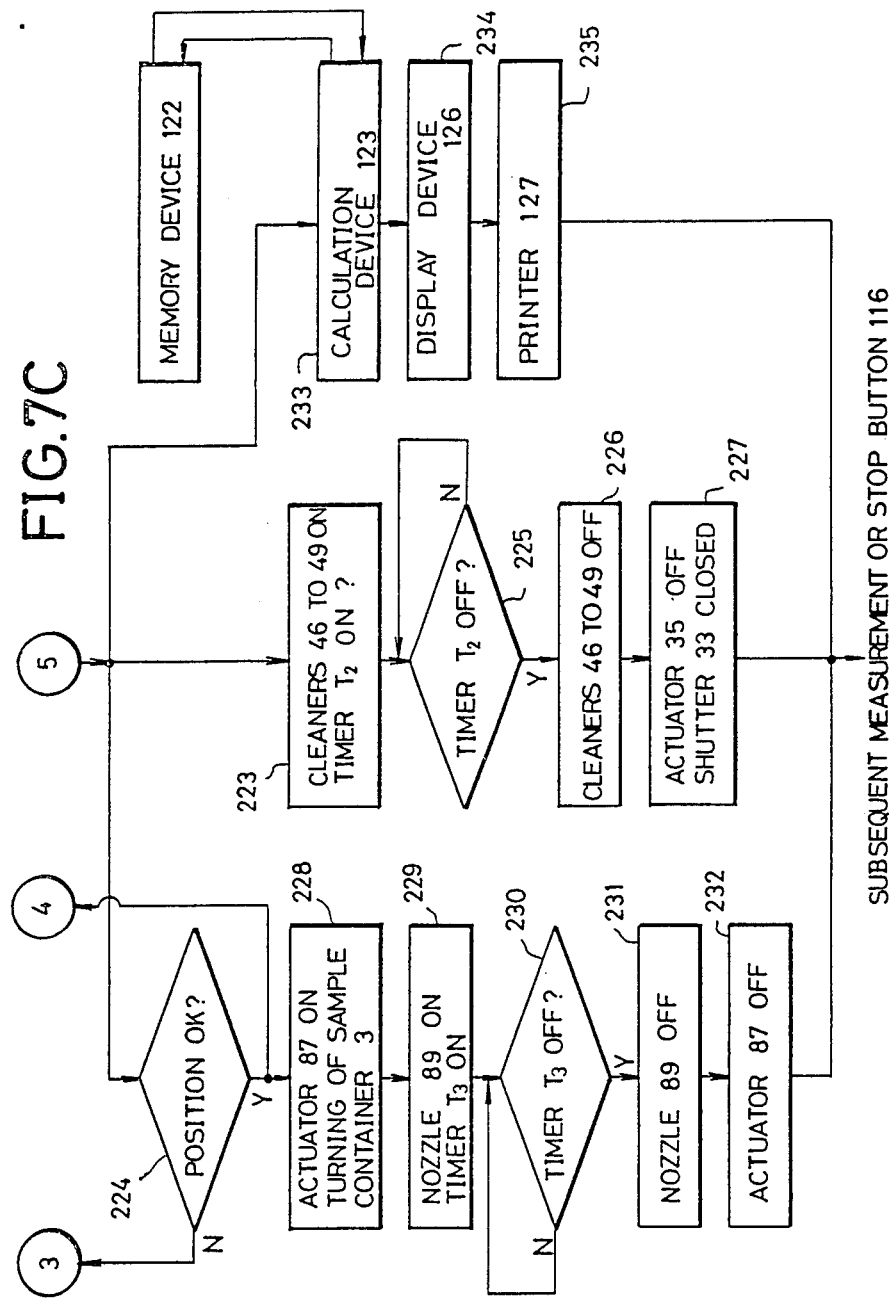

MEASURING APPARATUS FOR AMYLOSE AND/OR AMYLOPECTIN CONTENT IN RICE

CROSS REFERENCE TO A RELATED APPLICATION

The invention is related to U.S. Ser. No. 24,139 entitled "Apparatus For Evaluating The Quality Of Rice Grains" filed on Mar. 10, 1987 in the name of Toshihiko SATAKE assigned to the assignee of this invention.

BACKGROUND OF THE INVENTION

The present invention relates to an apparatus for measuring amylose and/or amylopectin content in rice.

This invention is particularly suitable for use in an apparatus for evaluating the quality of rice grains as disclosed in the applicant's prior application, U.S. Ser. No. 24,139. By reference to the applicant's prior application, the disclosure therein is incorporated in this specification.

Amylose or amylopectin content in starch has conventionally been measured by the use of a chemical method such as iodine colorimetric method or ioometric electric current titration method.

The above chemical method has such problems that considerable skill is required for measurement, variation in measurement results is large, and a long time is necessary for measurement. The reason for this is that the amylose and amylopectin contained in rice are approximate in composition to each other in that both of them are an isomer of a substance in which several hundreds of grape sugar molecules $C_6H_{12}O_6$ are coupled to each other.

SUMMARY OF THE INVENTION

It is an object of the invention to provide a measuring apparatus by which amylose and/or amylopectin content in rice can be easily and accurately measured.

According to the invention, there is provided an apparatus for measuring amylose and/or amylopectin content in rice, the apparatus comprising:

a sample container located at a predetermined measuring position with sample rice to be measured being contained in the sample container;

a near infrared spectrometer including a light source for applying light to the sample rice, optical means located between the light source and the sample rice for permitting passage of a near infrared light beam having its wavelength within a range of from about 1900 nm to about 2500 nm, of the light from the light source, and luminous intensity detecting means for detecting luminous intensity of the light reflected from and/or transmitted through the sample rice to generate signals representative of the luminous intensity;

control means including memory means for storing therein content conversion coefficients set for the amylose and/or amylopectin, and calculation means for calculating the amylose and/or amylopectin content in the sample rice, based on the content conversion coefficients and the signals from the luminous intensity detecting means; and display means connected to the control means for displaying the amylose and/or amylopectin content calculated by the calculation means.

BRIEF DESCRIPTION OF THE DRAWINGS

FIG. 2 is an enlarged cross-sectional view taken along line II—II in FIG. 1, showing in detail a near infrared spectrometer illustrated in FIG. 1;

FIG. 3 is a graph of absorbance curves showing the relationship between the wavelengths of near infrared light beam and the absorbance with respect to various varieties of rice;

FIG. 4 is a perspective view of transport means illustrated in FIG. 1 for reciprocating a sample container between a filling position and a measuring position;

FIG. 5 is a front elevational view of the measuring apparatus shown in FIG. 1;

FIG. 6 is a block diagram of a control unit incorporated in the measuring apparatus shown in FIG. 1;

FIGS. 7A–7C are a flow chart showing the operation of the measuring apparatus illustrated in FIG. 1;

DETAILED DESCRIPTION

The invention will now be described, by way of mere examples, with reference to the accompanying drawings.

Figure 1:
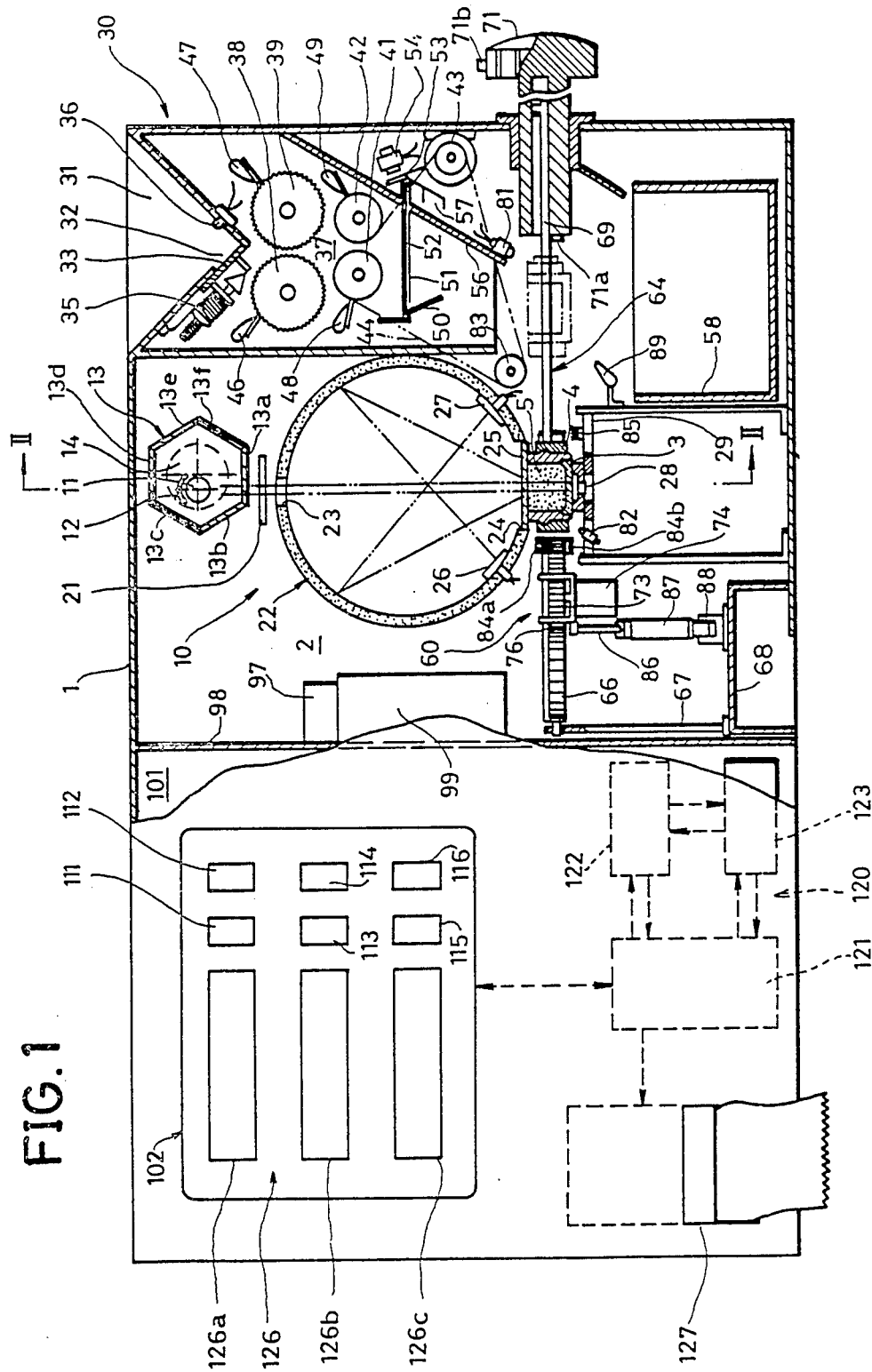
FIG. 1 is a front elevational view, partially broken away, of a measuring apparatus for amylose and amylopectin contents in rice, according to an embodiment of the invention.

Referring first to FIG. 1, there is schematically illustrated a measuring apparatus for amylose and amylopectin contents in rice, according to an embodiment of the invention. The measuring apparatus comprises a cabinet 1 generally in the form of a parallelpiped, which defines therein a measuring chamber 2. A sample container 3 having a transparent bottom wall is held by a holder 4 at a predetermined measuring position in a lower portion of the measuring chamber 2. The sample container 3 has received therein sample rice 5 to be measured which has been ground to have a particle size equal to or less than 500 micron meters, preferably, of approximately 50 micron meters.

Incorporated in the measuring chamber 2 is a near infrared spectrometer generally designated by the reference numeral 10 in FIGS. 1 and 2. The near infrared spectrometer 10 comprises a light source 11, such as a halogen lamp, which is mounted to a rear wall of the cabinet 1 in an upper portion of the measuring chamber 2. A concave reflecting mirror 12 is so positioned with respect to the light source 11 as to reflect the light from the light source 11 to any desired direction. An optical filter assembly 13 constituting optical means is drivingly connected to a stepping motor 14 mounted to the rear wall of the cabinet 1. The filter assembly 13 is comprised of six optical filters 13a to 13f arranged in the form of a regular hexagon about the light source 11. The optical filter assembly 13 is angularly moved stepwise by the stepping motor 14 by a predetermined angle so that selected one of the six optical filters 13a to 13f can be aligned with the optical axis of the light from the light source 11, and so that it is possible to optionally adjust a crossing angle between the face of the selected optical filter and the optical axis of the light from the light source 11. First one 13a of these optical filters has its nominal wavelength of a wavelength band from 1900 to 1970 nm; second one 13b, 2000 to 2060 nm; third one 13c, 2070 to 2130 nm; fourth one 13d, 2150 to 2200 nm; fifth one 13e, 2210 to 2260 nm; and sixth one 13f, 2270 to 2370 nm. A "nominal wavelength" is the maximum passing wavelength of the near infrared light beam which passes through an optical filter when the optical axis of the incident light beam is at right angles to the face of the optical filter.

The physical properties required for the optical filters 13a to 13f will now be described with reference to FIG. 3 which is a graph of absorbance curves showing the relationship between the wavelengths of illuminating light beam and the absorbance when the near infrared light beam whose wavelength is continuously varied is applied to different samples of rice. What is "absorbance" is the common cologarithm of the reference luminous intensity (entire luminous intensity) $I_0$ of the illuminating light beam to the luminous intensity I of the light beam reflected from or transmitted through the sample rice, that is log $I_0/I$. The curve A indicated by the solid line represents the rice variety "Nihonbare" whose amylose content is 21.4%, the curve B indicated by the dot-and-dash line represents the variety "Koshihikari" whose amylose content is 19.9% and the curve C indicated by the broken line represents the variety "Ishikari" whose amylose content is 23.2%. The "content" is the ratio with respect to 100% of rice starch. It will readily be seen from FIG. 3 that the short wavelength of near infrared light below 1900 nm is a region of low absorbance in which there are only slight differences in the absorbance, and with the 1900 nm as a dividing line, the long wavelength of the near infrared is a region of high absorbance in which marked differences in the absorbance are noted with the differences in the amylose content. Similar properties are represented also for amylopectin. The present invention utilizes this phenomenon or these properties to measure the amylose and/or amylopectin content in rice.

The near infrared spectrometer 10 further comprises a slit member 21 located below the optical filter assembly 13, and an integrating sphere 22 located below the slit member 21. The integrating sphere 22 is provided with a light intake window 23 opening at the slit member 21, and a measuring window 24 located in diametrically opposite relation to the light intake window 23 and opening at the aforesaid measuring position. The measuring window 24 is sealingly closed by a transparent plate 25 such as silica glass or the like to prevent dirt or dust from entering the integrating sphere 22. A pair of luminous intensity detecting elements 26 and 27 are fixedly arranged within the integrating sphere 22 at respective positions symmetric to each other with respect to the measuring window 24. A further luminous intensity detecting element 28 is fixedly supported at the measuring position on a support rod 29. The light from the light source 11 becomes a near infrared monochromatic light beam having specific wavelength after having passed through a selected one of the six optical filters 13a to 13f, and enters the integrating sphere 22 through the light intake window 23 thereof. The near infrared monochromatic light beam having entered the integrating sphere 22 is applied vertically to the sample rice 5 within the sample container 3 through the transparent plate 25 which closes the measuring window 24. A part of the light having entered the integrating sphere 22 is reflected from the sample rice 5, is then reflected from the inner wall surface of the integrating sphere 22, and finally reaches the pair of luminous intensity detecting elements 26 and 27. Thus, the luminous intensity of the reflected light is detected by the elements 26 and 27. In addition, the remaining part of the light having entered the integrating sphere 22 is transmitted through the sample rice 5 and the transparent bottom wall of the sample container 3, and reaches the luminous intensity detecting element 28. Thus, the luminous intensity of the transmitted light is detected by the element 28.

A sample supply mechanism, generally indicated by the reference numeral 30, is incorporated in the right hand end of the cabinet 1. The sample supply mechanism 30 comprises a hopper 31 mounted to an upper portion of the right hand end of the cabinet 1. The hopper 31 is provided at its bottom with a discharge port 32 which is adapted to be opened and closed by a slidable shutter 33. A solenoid actuator 35 mounted to the side wall of the hopper 31 is connected to the shutter 33 to slide the same for opening and closing the discharge port 32. A level sensor 36 is attached to the side wall of the hopper 31, for detecting the level of polished rice or brown rice to be ground, which rice is received in the hopper 31. Grinding means is arranged in a grinding chamber 37 below the discharge port 32. The grinding means includes a first pair of grinding rollers 38 and 39 rotatable about their respective rotary axes spaced in parallel relation to each other. Each of the rollers 38 and 39 has a roughened circumferential surface. The grinding means further includes a second pair of grinding rollers 41 and 42 rotatably arranged below the first pair of grinding rollers 38 and 39. The second pair of grinding rollers 41 and 42 have their respective axes spaced in parallel relation to each other, and each roller 41, 42 has a smooth circumferential surface. The roller 38 of the first pair of rollers is drivingly connected to the roller 41 of the second pair of rollers by means of gears, belt or the like. The roller 41 of the second pair of rollers is drivingly connected to a motor 43 fixedly mounted to the side wall of the cabinet 1, through a belt 44. Thus, when the roller 41 of the second pair of rollers is rotated by the motor 43, the roller 38 of the first pair of rollers drivingly connected to the roller 41 is also rotated. When rotated, the first pair of grinding rollers 38 and 39 finely grind the rice supplied to the nip therebetween through the discharge port 32 of the hopper 31. When rotated, the second pair of grinding rollers 41 and 42 further finely grind the ground rice supplied to the nip therebetween through the nip between the first pair of rollers 38 and 39. The rollers 38, 39, 41 and 42 have associated therewith respective cleaning devices 46, 47, 48 and 49 each of which is comprised of a nozzle with electromagnetic valve for blowing compressed air against the circumferential surface of the corresponding roller and a blade which is formed of elastic material and which is in sliding contact with the corresponding roller. A vibratory screening device 50 is arranged below the second pair of grinding rollers 41 and 42, and comprises a vibratory frame 51 and a screen 52 mounted thereto and having meshes below 500 micron meters. The vibratory frame 51 is mounted to the side wall of the cabinet 1 through two leaf springs 53. The vibratory frame 51 has an upstanding end wall toward which an electromagnet 54 is disposed to face. When energized, the electromagnet 54 vibrates the vibratory frame 51 and the screen 52 mounted thereto. The rice ground by the second pair of grinding rollers 41 and 42 falls onto the screen 52. Sample rice to be measured having a desired particle size, which has passed through the meshes of the screen 52, is fed to a predetermined filling position by a guide chute 56 mounted to the side wall of the cabinet 1. Rice remaining on the screen 52 passes through a discharge chute 57 attached to the vibratory frame 51, and is received in a container 58 which is capable of being taken in and out through a front wall of the measuring chamber 2.

The aforementioned sample container 3 detachably held by the holder 4 is provided with a grip 7 as shown in FIG. 4. The holder 4 is generally in the form of the letter U, and has two legs formed respectively with guide grooves. On the other hand, the opposite sides of the sample container 3 is formed respectively with elongated projections 8 which are frictionally fitted respectively in the guide grooves. Thus, the sample container 3 can be detachably held by the holder 4.

The holder 4 is movable between the aforesaid measuring and filling positions by transport means generally designated by the reference numeral 60 in FIG. 1. The transport means 60 comprises a carriage 63 as shown in FIG. 4, and the holder 4 is mounted on the carriage 63 for angular movement therewith. The carriage 63 is mounted on a guide rail 64 having a circular cross-section in such a manner that the carriage 63 is slidable along the guide rail 64 and angularly movable thereabout. The guide rail 64 has one end 66 thereof which is supported by a support leg 67 mounted on a table 68 which is in turn fixed to the bottom wall of the cabinet 1, as shown in FIG. 1. The other end 69 of the guide rail 64 is fitted in a manual turning handle 71 in such a manner that the guide rail 64 is angularly movable with the turning handle 71, but the turning handle 71 is axially movable along the guide rail 64. The manual turning handle 71 is rotatably and slidably mounted through the side wall of the cabinet 1. The turning handle 71 has its distal end provided with a latch 71a which is operated by a button 71b at the proximal end of the turning handle 71. The latch 71a is engageable with a hook 9 (see FIG. 4) provided on the leg of the holder 4. Referring again to FIG. 4, the carriage 63 is integrally formed with a rack 72 extending along the axis of the carriage 63. A pinion 73 in mesh with the rack 72 is fixedly mounted on an output shaft of a reversible motor 74. The motor 74 is mounted to a bracket 76 which is mounted on the carriage 63 in such a manner that the bracket 76 is angularly movable with the carriage 63, but the carriage 63 is axially movable with respect to the bracket 76. When the motor 74 is energized, the pinion 73 in mesh with the rack 72 is rotated so that the carriage 63 is reciprocated along the guide rail 64. Thus, the holder 4 secured to the carriage 63 is capable of being reciprocated between the filling position, indicated by the two-dot-and-dash lines in FIG. 1, where the sample rice falling along the guide chute 56 is filled in the sample container 3, and the measuring position where the sample container 3 is located at the measuring window 24 of the integrating sphere 22.

As shown in FIG. 5, the front wall of the cabinet 1 is provided with an opening 77 closable by a cover 78. The sample container 3 may be filled with the sample rice 5 which has been ground by an external grinding device separate from the grinding rollers 38, 39, 41 and 42 of the aforementioned sample rice supply mechanism 30. In this case, the sample container 3 filled with the sample rice 5 can be mounted to and dismounted from the holder 4 through the opening 77.

As shown in FIG. 1, a position sensor 81 attached to the guide chute 56 detects whether the holder 4 is located at the filling position, to generate signals. A position sensor 82 secured to the support rod 29 having attached thereto the luminous intensity detecting element 28 detects whether the holder 4 is located at the predetermined measuring position, to generate signals. When the holder 4 moves from the filling position to the measuring position, a roller 83 rotated by the motor 43 through the belt 44 is brought into rolling contact with the top of the sample container 3 held by the holder 4 to compressively fill the sample rice into the sample container 3, and to remove excessive sample rice from the sample container 3. Moreover, as shown in FIG. 4, first and second cleaners 84a and 84b formed by synthetic resin brushes or the like are secured to the carriage 63 adjacent the holder 4. When the holder 4 is moved between the filling and measuring positions, the first and second cleaners 84a and 84b are brought respectively into sliding contact with the lower surface of the transparent plate 25 closing the measuring window 24 of the integrating sphere 22 and the surface of the luminous intensity detecting element 28, to respectively clean the plate 25 and the element 28. Furthermore, a third cleaner 85 similar in construction to the first and second cleaners 84a and 84b is fixedly mounted on the beforesaid support rod 29 on which the luminous intensity detecting element 28 is fixedly supported. When the holder 4 is moved between the filling and measuring positions, the lower surface of the transparent bottom wall of the sample container 3 is brought into sliding contact with the third cleaner 85, whereby the transparent bottom wall is cleaned.

As clearly shown in FIG. 4, a telescopic rod 86 of a solenoid actuator 87 constituting turning means has a forward end which is pivotally connected to the bracket 76 on which the motor 74 is mounted. The actuator 87 is pivotally supported by a pivot stand 88 secured to the table 68 shown in FIG. 1. When the solenoid actuator 87 is energized, the rod 86 is withdrawn to angularly move the bracket 76, hence the carriage 63 by 90 degrees about the axis of the guide rail 64. Thus, as the actuator 87 is energized when the holder 4 occupies the filling position, the sample container 3 held by the holder 4 is angularly moved through 90 degrees about the axis of the guide rail 64, thereby permitting the sample rice 5 to freely fall from the sample container 3. A nozzle 89 provided adjacent the filling position is arranged to blow compressed air against the sample container 3 after the latter has been angularly moved by 90 degrees, to blow off the sample rice from the sample container 3, to thereby clean the interior thereof.

As clearly shown in FIG. 2, a temperature sensor 93 such as a thermistor is attached to the sample container 3 to detect temperature of the sample rice 5 received therein. The temperature sensor 93 is connected to a contact 94 which is adapted to be brought into sliding contact with a contact 96 secured to the integrating sphere 22 when the sample container 3 held by the holder 4 occupies the measuring position.

As shown in FIG. 1, a temperature sensor 97 for detecting temperature within the measuring chamber 2 is attached to a central partition wall 98 defining the measuring chamber 2 within which the near infrared spectrometer 10 is arranged. A temperature regulator 99 mounted to the central partition wall 98 is operative in response to signals from the temperature sensor 97, to regulate the temperature within the measuring chamber 2, hence various components of the near infrared spectrometer 10 to a predetermined value.

A control chamber 101 is defined within the cabinet 1 by the central partition wall 98. An operation panel 102 is attached to a front wall of the control chamber 101. The operation panel 102 has arranged thereon a manual operation button 111 for manually operating the measuring apparatus, an automatic operation button 112 for automatically operating the measuring apparatus, a transmitted luminous intensity selector button 113 for selecting the operation of only the luminous intensity detecting element 28, a reflected and transmitted luminous intensity selector button 114 for selecting the operation of the pair of luminous intensity detecting elements 26 and 27 within the integrating sphere 22 in addition to the luminous intensity detecting element 28, a start button 115 and a stop button 116.

The control chamber 101 has incorporated therein a control unit generally designated by the reference numeral 120, subsequently to be described in detail with reference to FIG. 6. The control unit 120 comprises an input-output signal processing device 121, a memory device 122 connected thereto, and a calculation device 123 connected to the signal processing device 121 and the memory device 122. The input-output signal processing device 121 is connected to various components of the aforementioned near infrared spectrometer 10, the sample rice supply mechanism 30 and the transport means 60, and to the operation buttons 111 to 116. The memory device 122 has stored and set therein content conversion coefficients, a temperature setting value, temperature correction values and operating procedures. The calculation device 123 calculates and corrects the amylose and amylopectin contents in rice, based on the signals from the luminous intensity detecting elements 26, 27 and 28 of the near infrared spectrometer 10, and the content conversion coefficients, the temperature correction values and the reference luminous intensities stored in the memory device 122. Connected to the input-output signal processing device 121 are a display device 126 of LED or CRT type mounted to the operating panel 102, and a printer 127 incorporated in the control chamber 101. The display device 126 is comprised of a display unit 126a for visually displaying the operating procedures of the measuring apparatus, a display unit 126b for visually displaying the amylose content and a display unit 126c for visually displaying the amylopectin content. The printer 127 prints out and displays the signals from the control unit 120.

The construction of the aforesaid control unit 120 will be described with reference to FIG. 6. Connected to the input side of the input-output signal processing device 121 are the operation buttons 111 to 116, the luminous intensity detecting elements 26, 27 and 28, the level sensor 36, the position sensors 81 and 82, the temperature sensors 93 and 97, and a keyboard 128. Connected to the output side of the input-output signal processing device 121 through respective drive units 130 to 139 are the light source 11, the temperature regulator 99, the stepping motor 14, the solenoid actuator 35, the motor 43, the cleaners 46 to 49, the electromagnet 54, the motor 74, the solenoid actuator 87 and the nozzle 89.

Figure 7A:
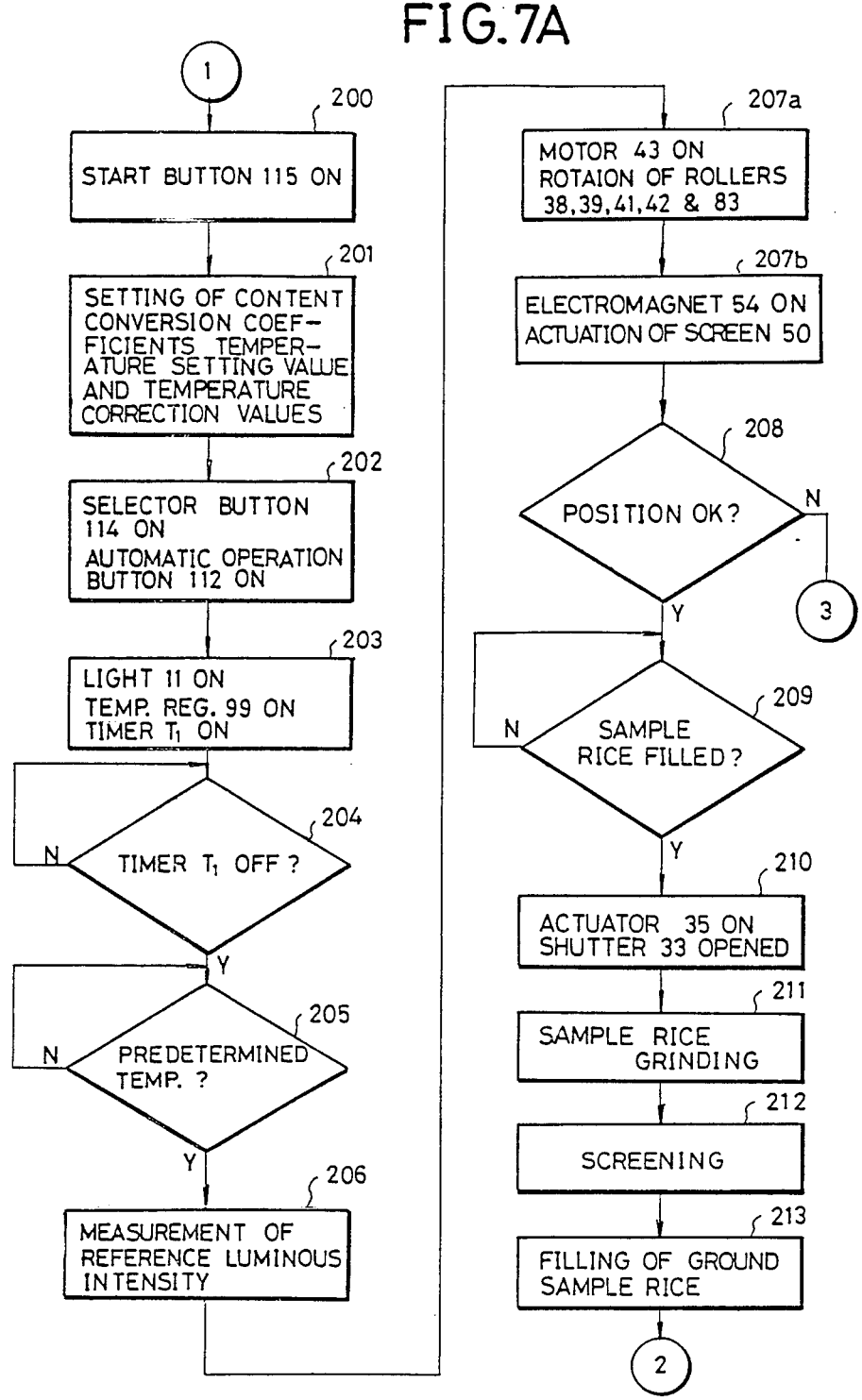
Figure 7B:
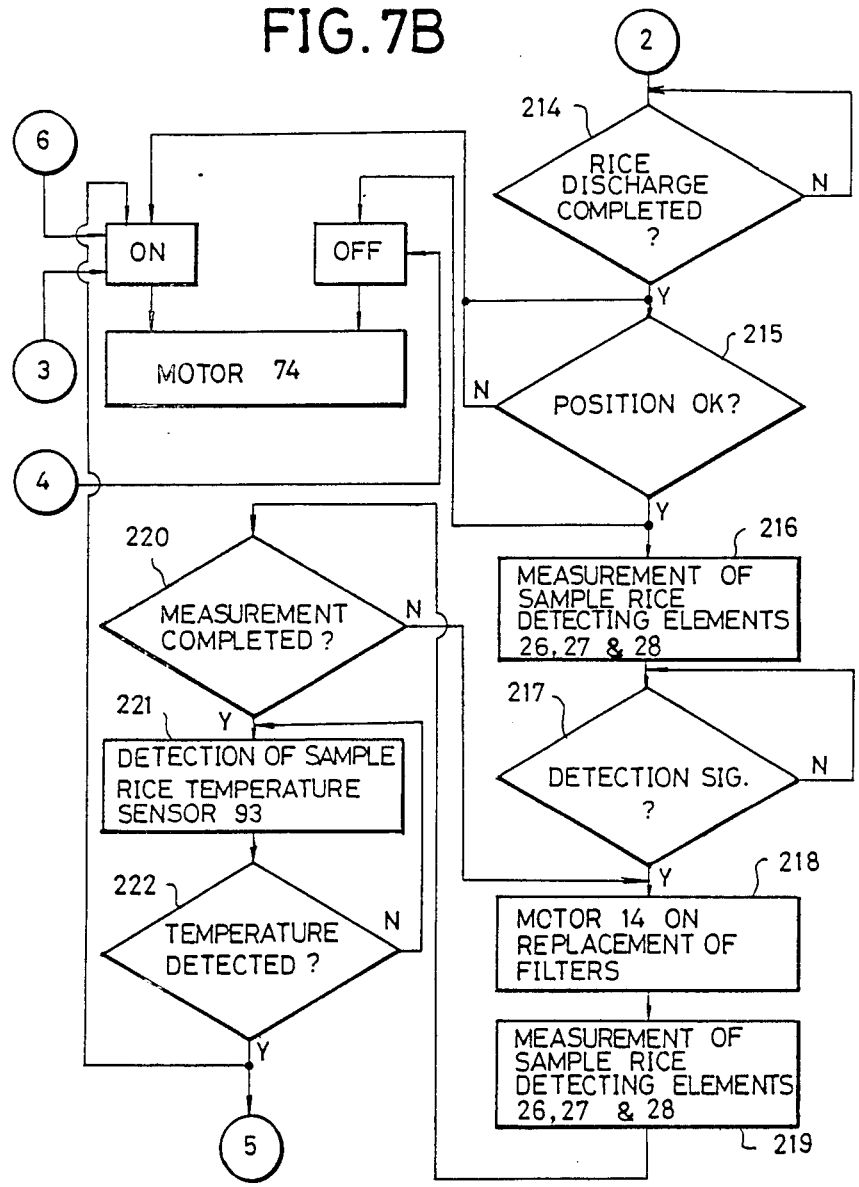

The operation of the measuring apparatus constructed as set forth above will now be described with reference to the flow chart shown in FIGS. 7A-7C. At a step 200, the start button 115 is depressed to turn on an electric power source. At a step 201, the keyboard 128 is operated to set and store the content conversion coefficients for calculating the amylose and amylopectin contents in the rice, the temperature setting value and the temperature correction values in the memory device 122 of the control unit 120. The content conversion coefficients are previously obtained by a multiple regression analysis (or also called a hypercomplex regression analysis) on signal-processed values of the detecting signals from the luminous intensity detecting elements 26, 27 and 28, based on amylose and amylopectin contents of a multiplicity of types of rice sample measured by a chemical quantitative analysis method such as iodine colorimetric method or iodometric electric current titration method.

An example of the multiple regression analysis on amylose will be described with reference to a case where a single optical filter whose nominal wavelength is 2100 nm, for example, is employed to conduct measurement. The following linear relationship is satisfied between the amylose content $C_s$ in sample rice and the absorbance X $(=\log I_0/I)$ based on the luminous intensities detected by the detecting elements of the near infrared spectrometer:

$$C_s = F_0 + F_1 \times X$$

where $F_0$ and $F_1$ are content conversion coefficients to be obtained by this multiple regression analysis.

When the absorbance X is measured by the use of the aforesaid optical filter having its nominal wavelength of 2100 nm, with respect to the known sample rice $S_1$ whose amylose content $C_s$ is 18.2%, the absorbance X is 0.68095. Likewise, when the respective absorbances X are measured with respect to the known samples $S_2$ whose amylose content $C_s$ is 19.5% and the known sample rice $S_3$ whose amylose content $C_s$ is 20.1%, the respective absorbances X are 0.65379 and 0.57493. If $F_0$ and $F_1$ are obtained by the multiple regression analysis based on these values $C_s$ and X, $F_0$ and $F_1$ are 39.05 and $-30.595$, respectively. These values $F_0$ and $F_1$ are stored in the memory device 122 of the control unit 120. The calculation device 123 calculates the amylose content $C_s$ in accordance with the following equation, based on the detecting signals from the luminous intensity detecting elements 26, 27 and 28 of the near infrared spectrometer 10 and the content conversion coefficients $F_0$ and $F_1$ stored in the memory device 122:

$$C_s = 39.05 - 30.595 \times X$$

Another example of the multiple regression analysis on amylose will be described next with reference to a case where five optical filters whose respective nominal wavelengths are 2100 nm, 2180 nm, 2230 nm, 2280 nm and 2310 nm are employed to conduct measurement. In this case, the following linear relationship is satisfied:

$$C_s = F_0 + F_1 \times X_1 + F_2 \times X_2 + F_3 \times X_3 + F_4 \times X_4 + F_5 \times X_5$$

where
$C_s$ is amylose content in sample rice,
$F_0$ to $F_5$ are content conversion coefficients to be obtained by this multiple regression analysis, and
$X_1$ to $X_5$ are respective absorbances (log $I_0/I$) measured by the use of five optical filters.

When the absorbances $X_1$ to $X_5$ are respectively measured by the use of the five optical filters, with respect to the known sample rice $S_4$ whose amylose content is 18.5%, $X_1$ to $X_5$ are 0.627605, 0.545498, 0.505677, 0.63974 and 0.66042, respectively. Likewise, when $X_1$ to $X_5$ are measured by the respective filters, with respect to the known sample rice $S_5$ whose amylose content $C_s$ is 19.0%, $X_1$ to $X_5$ are 0.602490, 0.523668, 0.486170, 0.625618 and 0.63556, respectively. Likewise, when $X_1$ to $X_5$ are measured by the respective filters, with respect to the known sample rice $S_6$ whose amylose content $C_s$ is 21.2%, $X_1$ to $X_5$ are 0.547453, 0.478355, 0.448358, 0.562407 and 0.58103, respectively. If $F_0$ to $F_5$ are obtained by the multiple regression analysis, based on these values $C_s$ and $X_1$ to $X_5$, $F_0=33.33$, $F_1=2382$, $F_2=-2306$, $F_3=-644.2$, $F_4=1406$ and $F_5=-882.6$.

The aforesaid values $F_0$ to $F_5$ are stored in the memory device 122. The calculation device 123 calculates the amylose content $C_s$ in the sample rice 5 in accordance with the following equation, based on the detecting signals from the luminous intensity detecting elements 26, 27 and 28 of the near infrared spectrometer 10 and the content conversion coefficients $F_0$ to $F_5$ stored in the memory device 122:

$$C_s=33.3+2383X_1-2306X_2-644.2X_3+1406X_4-88-2.6X_5$$

Content conversion coefficients for the amylopectin can be obtained in the same manner as that described above.

Figure 8:
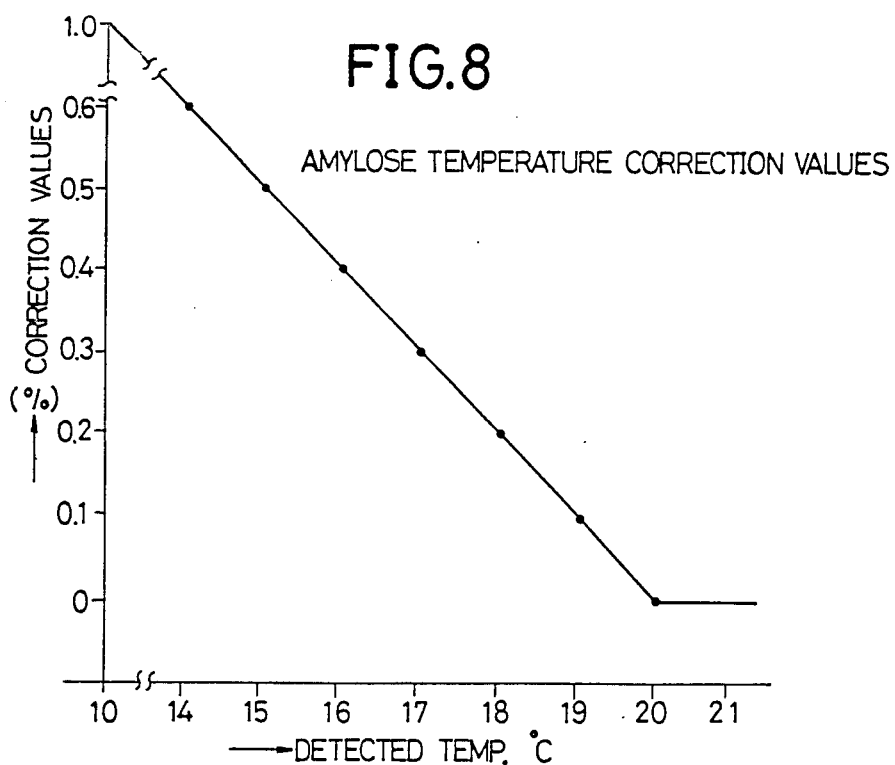
FIG. 8 is a graphical representation of temperature correction values with respect to calculated amylose values.

Absorption of the near infrared light beam applied to the sample rice, into the same is a phenomenon occurring due to vibration of the chains of atoms forming the molecules by thermal energy. Since the natural resonant frequency varies depending upon the kind of atoms and the chain conditions, the vibration changes in magnitude within the wavelength range of the near infrared light beam, so that the thermal absorption occurs. In addition, if the initial thermal energy of the sample rice is low, i.e., if the temperature thereof is low, the absorption amount due to the difference in the molecular structure cannot accurately be measured because the vibration is low in magnitude. Accordingly, it is necessary to correct the calculated results of the calculation device 123 in accordance with the temperature of the sample rice to be measured. FIG. 8 shows, as an experimental example, temperature correction values with which the measured amylose values are to be corrected, based on the detecting values of the temperature sensor 93 attached to the sample container 3. No correction is required for temperatures above 20° C. For a temperature of 10° C., however, an accurate or true value is obtained if 1.0% is added to the calculated results of the calculation device 123. The correction value changes generally linearly in a range between 10° and 20° C. Similar correction is required for amylopectin.

The temperature setting value stored in the memory device 122 is utilized to regulate the temperature of various components of the near infrared spectrometer 10, to a predetermined value, and is normally set to 25° C. The principal purposes of maintaining the temperature of the near infrared spectrometer 10 to the predetermined value is to prevent variations in temperature of the sample rice 5 in the sample container 3.

Next, as the reflected and transmitted luminous intensity selector button 113 and the automatic operation button 112 are depressed at a step 202, the near infrared spectrometer 10 is energized. At a step 203, the input-output signal processing device 121 sends an ON signal to the drive unit 130 to turn on the light source 11. A timer $T_1$ incorporated in the input-output signal processing device 121 is also turned on. The timer $T_1$ sets a period of time for which the near infrared monochromatic light of the specific wavelength based on the light from the light source 11 stabilizes. At the step 203, an ON signal is sent to the drive unit 131 to actuate the temperature regulator 99 for maintaining the various components of the near infrared spectrometer 10 to the predetermined value. At a step 204, as the time period set by the timer $T_1$ elapses, the input-output signal processing device 121 causes the program to proceed to a step 205 where the temperature sensor 97 detects whether the near infrared spectrometer 10 is brought to the temperature setting value stored in the memory device 122. In response to the signal from the temperature sensor 97 indicating that the near infrared spectrometer 10 is brought to the predetermined temperature, the program proceeds to a step 206 where the measurement of the reference luminous intensities $I_0$ is carried out. The measurement of the reference luminous intensities $I_0$ is performed in a manner similar to that of measuring the transmitted and reflected luminous intensities subsequently to be described in detail, and will be described here briefly. Firstly, a reference plate is carried onto the sample container 3 filled with no sample rice. The light source 11 applies the light to the reference plate through one of the six optical filters 13a to 13f and through the transparent plate 25 of the integrating sphere 22. The light reflected by the reference plate and further reflected by the inner wall surface of the integrating sphere 22 is received by the luminous intensity detecting elements 26 and 27 thereby measuring lminous intensity of the light, i.e., reflected reference luminous intensity. Similar measurements are performed through the remaining respective optical filters. In this manner, the reflected reference luminous intensities are measured which correspond respectively to the optical filters, and are stored in the memory device 122 of the control unit 120. Subsequently, the reference plate is removed out of the sample container 3. The light from the light source 11 is transmitted through the transparent plate 25 of the integrating sphere 22 and the transparent bottom wall of the sample container 3, and is received by the luminous intensity detecting element 28 thereby measuring luminous intensity of the transmitted light, i.e., transmitted reference luminous intensity. The transmitted reference luminous intensities are measured through the respective optical filters 13a to 13f. In this manner, the transmitted reference luminous intensities are measured and are stored in the memory device 122. The manner of measuring the reference luminous intensities is not limited to that described above, but various other ways can be used to measure the reference luminous intensities. Subsequent to the measurement of the reference luminous intensities $I_0$, the program proceeds to a step 207a where the input-output signal processing device 121 sends an ON signal to the drive unit 134 to turn on the motor 43, to thereby rotate the rollers 38, 39, 41 and 42 as well as the roller 83. At a subsequent step 207b, the input-output signal processing device 121 sends an ON signal to the drive unit 136 to energize the electromagnet 54, thereby actuating the vibratory screening device 50 so that the vibratory frame 51 is vibrated. At a step 208, the position sensor 81 detects whether or not the sample container 3 is located at the predetermined filling position. As the position sensor 81 detects that the sample container 3 is not located at the filling position, the input-output signal processing device 121 sends an ON signal to the drive unit 137 to turn on the motor 74, to thereby move the holder 4 having held thereon the sample container 3, along the guide rail 64. As the position sensor 81 detects that the sample container 3 is located at the filling position, the program proceeds to a step 209 where the level sensor 36 detects whether or not the rice is received in the hopper 31. If the detection indicates "YES", the program proceeds to a step 210 where the solenoid actuator 35 is turned on by the drive unit 133 to open the shutter 33, so that the rice is fed toward the nip between the first pair of grinding rollers 38 and 39 through the discharge port 32 of the hopper 31. The program proceeds to a step 211 where the rice from the hopper 31 is ground by the first pair of grinding rollers 38 and 39, and is further ground by the second pair of grinding rollers 41 and 42. Grinding of the rice by the first and second pairs of grinding rollers in the two step manner allows the ground rice particles to be sufficiently mixed with each other, to thereby enhance the measurement accuracy. At a subsequent step 212, the ground rice falls onto the vibratory screen 52 and is sorted thereby. At a step 213, sample rice to be measured of a desired particle size having passed through the meshes of the screen 52 falls into the sample container 3 located at the filling position, and is filled therein. Sample rice overflowing from the sample container 3 falls into the container 58. In addition, the relatively coarse ground rice falls also into the container 58 through the discharge chute 57.

At a step 214, the level sensor 36 detects whether or not the rice within the hopper 31 is completely discharged therefrom through the discharge port 32. If the detection indicates "YES", the input-output signal processing device 121 sends an ON signal to the drive unit 137 in response to the signal from the level sensor 36, to actuate the reversible motor 74. This causes the holder 4 having held thereon the sample container 3 to be moved toward the measuring position along the guide rail 64. When the holder 4 moves from the filling position toward the measuring position, the sample rice standing up above the rim of the sample container 3 held by the holder 4 is compressed by the rotating roller 83 so that the sample rice is filled under pressure into the sample container 3, and the upper surface of the sample rice within the sample container 3 is flattened. At this time, the sample rice overflowing from the sample container 3 falls into the container 58. At a step 215, the position sensor 82 detects whether or not the sample container 3 held by the holder 4 reaches the predetermined measuring position. If the detection indicates "YES", an OFF signal sent to the drive unit 137 causes the motor 74 to stop in operation. The program proceeds to a step 216 where the measurement by the near infrared spectrometer 10 is started in response to the "YES" signal from the position sensor 82.

At the outset, the motor 14 is turned on by the drive unit 132 to align selected one of the optical filters 13a to 13f, which has a desired nominal wavelength, with the optical axis of the light from the light source 11. The light from the light source 11 becomes the near infrared monochromatic light beam having the specific wavelength after having passed through the selected optical filter such as one designated by the reference numeral 13a. Subsequently, the light passes through the slit member 21 and the light intake window 23 of the integrating sphere 22, and enters the same. The light having entered the integrating sphere 22 is applied vertically to the sample rice 5 within the sample container 3. Luminous intensity of the light transmitted through the sample rice 5 is detected by the luminous intensity detecting element 28, and the signals therefrom are sent to the input-output signal processing device 121. Luminous intensity of the light reflected by the sample rice 5 and then reflected by the inner wall surface of the integrating sphere 22 is detected by the pair of luminous intensity detecting elements 26 and 27, and the signals therefrom are also sent to the input-output signal processing device 121. If it is desired to effect the measurement through a plurality of wavelength bands, the input-output signal processing device 121 is operative, at a step 217, in response to the signals from the luminous intensity detecting elements 26, 27 and 28, to cause the program to proceed to a step 218 where the motor 14 is turned on by the drive unit 132. The filter assembly 13 is angularly moved by the motor 14 in such a manner that the optical filters 13b to 13f are successively aligned with the optical axis of the light from the light source 11. Luminous intensity detection similar to that effected through the filter 13a is successively performed, at a step 219, by the luminous intensity detecting element 26, 27, and 28 through the respective filters 13b to 13f. Signals from the elements 26, 27 and 28 are successively sent to the input-output signal processing device 121. Each of the filters 13a to 13f has a half-width in a wavelength range of plus and minus 10 nm in the corresponding specific wavelength. The input-output signal processing device 121 judges, at a step 220, whether or not the detection is completed through the respective filters 13a to 13f. If the detection is not completed through all of the filters 13a to 13f, the program is returned to the step 218.

As the detection is completed through all of the filters 13a to 13f, the program proceeds to a step 221 where the temperature sensor 93 detects the temperature of the sample rice 5 within the sample container 3, and signals representative of the temperature are sent to the input-output signal processing device 121. At a step 222, the signal processing device 121 judges whether or not the temperature detection is conducted by the temperature sensor 93. If the judgment indicates "YES", the input-output signal processing device 121 turns on a timer $T_2$ incorporated therein at a step 223, and sends an ON signal to the drive unit 135 to actuate the cleaning devices 46 through 49, thereby cleaning the rollers 38, 39, 41 and 2. Moreover, the input-output signal processing device 21 sends an ON signal to the drive unit 137 to actuate the motor 74, to thereby move the holder 4 having held thereon the sample container 3, toward the filling position. As the position sensor 81 detects, at a step 24, that the sample container 3 reaches the predetermined filling position, the input-output signal processing device 121 sends an OFF signal to the drive unit 137 to stop the operation of the motor 74. When the holder 4 is moved toward the filling position, the first cleaner 84a is brought into sliding contact with the lower surface of the transparent plate 25 closing the measuring window 24 of the integrating sphere 22 to clean the transparent plate 25. In addition, the second cleaner 84b is brought into sliding contact with the surface of the luminous intensity detecting element 28 fixedly mounted on the support rod 29 to clean the element 28. Furthermore, the third cleaner 85 fixedly mounted on the support rod 29 is brought into sliding contact with the transparent bottom wall of the sample container 3 to clean the same. As the predetermined period of time set by the timer $T_2$ elapses at a step 225, the input-output signal processing device 121 sends, at a step 226, an OFF signal to the drive unit 135 to stop the operation of the cleaning devices 46 through 49. At a subsequent step 227, the input-output signal processing device 121 sends an OFF signal to the drive unit 133 to stop the operation of the solenoid actuator 35. This causes the shutter 33 to be moved to close the discharge port 32 of the hopper 31. As the position sensor 81 detects, at the aforementioned step 224, that the sample container 3 reaches the predetermined filling position, the input-output signal processing device 121 sends an ON signal to the drive unit 138 to actuate the solenoid actuator 87. The bracket 76 having carried thereon the motor 74 is angularly moved by the actuator 87 about the axis of the guide rail 64 through 90 degrees. At this time, the sample rice 5 within the sample container 3 falls therefrom into the container 58. At a subsequent step 229, the input-output signal processing device 121 turns on a timer $T_3$ incorporated therein, and sends an ON signal to the drive unit 139 to actuate the nozzle 89. Compressed air is blown through the nozzle 89 against the sample container 3 having angularly moved through 90 degrees, to blow off the sample rice 5 from the sample container 3 to clean the interior thereof. As the period of time set by the timer $T_3$ elapses at a step 230, the input-output signal processing device 121 sends an OFF signal to the drive unit 139 to stop the operation of the nozzle 89. At a step 232, an OFF signal is sent to the drive unit 138 to stop the operation of the solenoid actuator 87. The holder 4 located at the filling position is angularly moved through 90 degrees to the initial position, to prepare for a subsequent measurement of sample rice.

As mentioned previously, the detecting signals from the luminous intensity detecting elements 26, 27 and 28 and the detecting signals from the temperature sensor 93 are sent to the input-output signal processing device 121. At a step 233, the calculation device 123 of the control unit 120 calculates the amylose and amylopectin contents, based on the detecting signals from the luminous intensity detecting elements 26, 27 and 28, and the content conversion coefficients for the amylose and amylopectin, the temperature correction values and the reference luminous intensities stored in the memory device 122. The calculated amylose and amylopectin contents are stored in the memory device 122. In addition, the calculated amylose and amylopectin contents are digitally displayed respectively by the display units 126b and 126c on the operation panel 102, and are automatically printed out and displayed by the printer 127 at a step 235. If it is desired to stop the operation of the measuring apparatus, the stop button 116 is depressed.

Next, a case will be described where in place of depression of the automatic operation button 112, the manual operation button 111 is depressed to manually operate the measuring apparatus. In case of the manual operation, the turning handle 71 is first pushed slightly into the cabinet 1. The button 71b at the proximal end of the turning handle 71 is operated to cause the latch 71a at the distal end of the turning handle 71 to engage with the hook 9 on the holder 4. Subsequently, an operator pushes the holder 4 with the turning handle 71 toward the measuring position, to move the holder 4 having held thereon the sample container 3 from the filling position to the measuring position. Then, the cover 78 shown in FIG. 4 is removed to open the opening 77.

The operator clamps the grip 7 of the sample container 3 to dismount the same from the holder 4, and takes the sample container 3 out of the cabinet 1 through the opening 77. Ground sample rice is compressively filled in the sample container 3, and the top surface of the sample rice filled in the sample container 3 is flattened. Subsequently, the sample container 3 is put into the measuring chamber 101 through the opening 77, and the projections 8 on the sample container 3 are fitted respectively into the guide grooves in the holder 4. Thus, the sample container 3 is mounted on the holder 4 located at the measuring position. The cover 78 is then fitted in the opening 77 to close the same. Subsequently, the near infrared spectrometer 10 is operated to carry out measurement. After completion of the measurement, the turning handle 71 is pulled to move the holder 4 from the measuring position to the filling position. Once the holder 4 is located at the filling position, the turning handle 71 is turned to angularly move the holder 4, to allow the sample rice within the sample container 3 held by the holder 4 to fall into the container 58. Subsequently, the latch 71a at the distal end of the turning handle 71 is disengaged from the hook 9 on the holder 4. It is of course that the sample container 3 may be taken out of the cabinet 1 through the opening 77 after the measurement, to throw away the sample rice to any desired location.

In order to obtain accurate detecting values of the contents, the sample rice to be filled in the sample container 3 is required to have a low particle size. The particle size should be 500 micron meters or less, preferably, approximately 50 micron meters. The below table shows the relationship between the particle size of the ground sample rice and the accuracy of the measured values when the true content value is regarded as 100%.

| Measurement Number | Relationship Between Particle Size Of Ground Sample Rice And Measurement Accuracy | | | | |
|---|---|---|---|---|---|
| | Particle Size (micron meters) | | | | |
| | Not Ground | 1000 | 500 | 300 | 100 |
| 1 | ±5.2 | ±2.4 | ±0.5 | ±0.2 | ±0.1 |
| 2 | ±5.0 | ±2.6 | ±0.5 | ±0.2 | ±0.1 |
| 3 | ±5.3 | ±2.2 | ±0.4 | ±0.1 | ±0.1 |
| 4 | ±4.7 | ±2.3 | ±0.5 | ±0.2 | ±0 |
| 5 | ±5.3 | ±2.4 | ±0.4 | ±0.2 | ±0.1 |
| Average | ±5.1 | ±2.2 | ±0.5 | ±0.2 | ±0.1 |

(Unit: %)

As will be seen from the above table, the measurement accuracy varies depending upon the particle size. It desirable that the measurement accuracy is ±0.5% or less. Accordingly, it is necessary to employ the screen 52 of the screening device 50 for sorting the ground sample rice, which screen has the meshes less than 500 micron meters. Likewise, also in case where sample rice is ground by the external grinding device which is not incorporated in the measuring apparatus shown in FIG. 1; the ground sample rice is filled in the sample container 3; and the sample container 3 is mounted on the holder 4 through the opening 77 shown in FIG. 4 to carry out the measurement, the measurement accuracy can be ensured if the ground sample rice is screened and only the sample rice having the particle size less than 500 micron meters is filled in the sample container 3. The reason for this is that as the size of the starch molecules is approximately 10 micron meters, the starch molecules do not uniformly appear on the upper surface of the sample container unless the sample rice is ground to have the particle size less than 500 micron meters; and, therefore, the vibration of the molecules due to the near infrared light beam is not performed accurately.

As described previously, the crossing angle between selected one of the six filters 13a to 13f of the filter assembly 13 and the optical axis of the illuminating light from the light source 11 can be adjusted to any desired value by the operation of the motor 14 in response to the signals from the input-output signal processing device 121 of the control unit 120. Although it is basic or fundamental that the selected filter be used at such a position that its face is perpendicular to the optical axis of the illuminating light, it is possible to slide the transmitted nominal wavelength of the selected filter through an optional wavelength by changing the crossing angle of the filter to the optical axis of the illuminating light. The wavelength transmitted when the selected filter has its face perpendicular to the optical axis of the illuminating light is different from that when the selected filter has its face intersecting the optical axis at any angles other than 90 degrees. As the crossing angle becomes smaller than 90 degrees, the transmitted nominal wavelength slides toward the short wavelength. Within a near infrared light beam range of from 1900 nm to 2500 nm, the effective transmitted nominal wavelength usually slides by 70 nm, if the filter's face shifts from 90 degrees with respect to the optical axis of the illuminated light. Accordingly, the crossing angle of the selected filter's face with respect to the optical axis of the illuminating light can be adjusted substantially continuously in order to enable continuous measurement within the range of from 1900 nm to 2500 nm.

Although the embodiment illustrated in FIG. 1 employs six filters 13a to 13f, it is needless to say that the measurement may be effected by the use of a single filter. In this case, the incident angle of the light from the light source to the single filter may be fixed or variable.

Although the embodiment has been described, for convenience, as having the measurement carried out based on the detecting signals from the luminous intensity detecting elements 26 and 27 as well as the luminous intensity detecting element 28, only the elements 26 and 27 may be employed, or only the element 28 may be employed. In the latter case, the transmitted luminous intensity selector button 113 is depressed to conduct the measurement. In addition, an external temperature sensor for detecting temperature of the exterior of the cabinet 1 may be substituted for the temperature sensor 97 for detecting the temperature within the measuring chamber 2. In this case, the temperature regulator 99 is operated in response to signals from the external temperature sensor.

Although the embodiment has been described as measuring both the amylose and amylopectin contents, only one of the amylose and amylopectin contents may be measured and displayed. In this case, the other can be obtained by the following equation:

$$C_1 + C_2 = 100\%$$

where $C_1$ is the amylose content, and
$C_2$ is the amylopectin content.

It is of course that if only one of the amylose and amylopectin contents is measured and displayed, one of the display units 126b and 126c of the display device 126 can be dispensed with. Further, it is needless to say that the detected values of the amylose or amylopectin do not necessarily need a purity of 100%.

Although the embodiment has been described as having the content conversion coefficients, temperature setting value and temperature correction values inputted by the keyboard 128, the keyboard 128 is not necessarily required, if these values are previously stored in a read only memory within the memory device 122. Further, the printer 127 need not be limited to the illustrated built-in type, but may be of externally connectable type. Moreover, although the embodiment has been described as having the pair of luminous intensity detecting element 26 and 27 arranged within the integrating sphere 22 for the purposes of enabling the compensation for the optical symmetry and facilitating efficient receiving of the reflected light from the sample rice 5, the number of the elements need not be limited to two, but one or three or more elements may be arranged within the integrating sphere 22. Furthermore, the measurement accuracy can further be ensured, if the detection of luminous intensity of the reflected light and the transmitted light is repeated in several times with respect to each of the optical filters 13a to 13f of the optical filter assembly 13 and the average value is taken.

Figure 9:
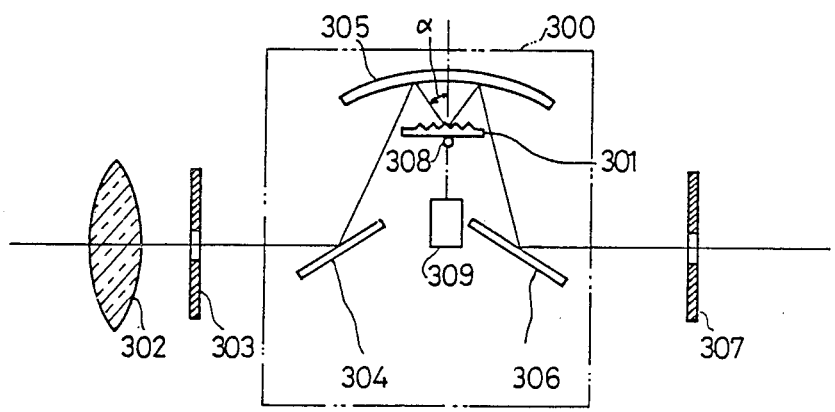
FIG. 9 is a diagrammatic view showing another embodiment of the invention which is designed to conduct continuous measurement within a wavelength range of from 1900 nm to 2500 nm.

FIG. 9 is a diagrammatic view showing another embodiment of the invention which is designed to carry out continuous measurement within a range of about 1900 nm to about 2500 nm. An optical system 300 used in this embodiment comprises a spectral element 301 which utilizes a diffraction grating. Illuminating light from a light source similar to the light source 11 shown in FIG. 1 is condensed by a condenser lens 302, and a part of the light passes through a slit member 303 and is applied to an incoming mirror 304. The light reflected from the incoming mirror 304 is further reflected from a concave reflecting mirror 305, and is incident upon the spectral element 301 at an optional incident angle $\alpha$. The light incident upon the spectral element 301 is reflected thereby, is further reflected by the concave reflecting mirror 305, and is incident upon an outcoming mirror 306. The light incident upon the outcoming mirror 306 has optional wavelength in accordance with the aforesaid angle $\alpha$. The light reflected by the outcoming mirror 306 is applied to the sample rice through a slit member 307. The spectral element 301 is mounted for pivotal movement about an axis of a pivot 308 which is drivingly connected to a reversible motor 309. Thus, control of the operation of the reversible motor 309 enables continuous change of the angle of the spectral element 301 with respect to the reflecting mirror 305, i.e., the incident angle $\alpha$.

Measurement of amylose or amylopectin content in rice by the use of the conventional chemical quantitative analysis has been troublesome in operation, and has required considerable time and skill. The reason for this is, as also stated previously, that both the amylose and amylopectin have their respective molecule formulae of combination of two hundreds to five hundreds of grape sugar $C_6H_{12}O_6$, and are merely different from each other in the linkage structure as a so-called isomer. The present invention has found the new fact that the difference in amylose or amylopectin content remarkably appears as an absorbance difference, in the near infrared light beam within a range of about 1900 nm to about 2500 nm. The invention measures the amylose and/or amylopectin content, based on the absorbance difference. Consequently, the measured values are accurate, and anyone can easily and quickly carry out the measurement.

What is claimed is:

1. An apparatus for measuring amylose and/or amylopectin content in rice, said apparatus comprising:
   a sample container located at a predetermined measuring position with sample rice to be measured being contained in said sample container;
   a near infrared spectrometer including a light source for applying light to said sample rice, optical means located between said light source and said sample rice for permitting passage of near infrared light beam having its wavelength within a range of from 1900 nm to 2500 nm, of the light from said light source, and luminous intensity detecting means for detecting luminous intensity of the light reflected from and/or transmitted through said sample rice to generate signals representative of the luminous intensity;
   control means including memory means for storing therein content conversion coefficients set for the amylose and/or amylopectin, and calculation means for calculating the amylose and/or amylopectin content in said sample rice, based on the content conversion coefficients and said signals from said luminous intensity detecting means; and
   display means connected to said control means for displaying the amylose and/or amylopectin content calculated by said calculation means.

2. An apparatus according to claim 1, wherein said optical means comprises optical filter means.

3. An apparatus according to claim 2, including:
   drive means drivingly connected to said optical filter means for driving the same to adjust an incident angle of the light from said light source incident upon said optical filter means.

4. An apparatus according to claim 2, wherein said optical filter means comprises at least one optical filter whose nominal wavelength is one of wavelength bands of 1900 to 1970 nm, 2000 to 2060 nm, 2070 to 2130 nm, 2150 to 2200 nm, 2210 to 2260 nm, and 2270 to 2370 nm.

5. An apparatus according to claim 2, including:
   said optical filter means comprising a plurality of optical filters different in nominal wavelength from each other; and
   drive means drivingly connected to said optical filter means for driving the same to align selected one of said plurality of optical filters with an optical axis of the light from said light source.

6. An apparatus according to claim 5, wherein said drive means is arranged to drive said optical filter means so as to adjust an incident angle of the light from said light source incident upon the selected optical filter.

7. An apparatus according to claim 6, wherein said optical filter means comprises six optical filters arranged generally in the form of a hexagon around said light source.

8. An apparatus according to claim 1, wherein said optical means comprises a reflecting mirror reflecting the light from said light source, a spectral element for spectra-diffracting the reflected light from said reflecting mirror, and adjusting means connected to one of said reflecting mirror and said spectral element for pivotally moving the same about a pivotal axis to vary a relative position between said reflecting mirror and said spectral element, to thereby adjust an incident angle of the light from said reflecting mirror incident upon said spectral element.

9. An apparatus according to claim 1, including:
   temperature detecting means for detecting temperature of said sample rice within said sample container to generate detecting signals;
   said memory means of said control means storing temperature correction values set for the amylose and/or amylopectin; and
   said calculation means of said control means correcting said amylose and/or amylopectin content, based on the detecting signals from said temperature detecting means and the temperature correction values stored in said memory means.

10. An apparatus according to claim 1, including:
    temperature detecting means for detecting temperature within a measuring chamber within which said near infrared spectrometer is disposed, for generating signals; and
    temperature regulating means for regulating temperature of various components of said near infrared spectrometer to a predetermined value, based on the detecting signals from said temperature detecting means.

11. An apparatus according to claim 1, including:
    said near infrared spectrometer comprising an integrating sphere having a light intake window through which the light from said light source passes, and a measuring window which is provided at a location diametrically opposite to said light intake window and which opens at said predetermined measuring position; and
    a holder disposed at said predetermined measuring position for detachably holding said sample container.

12. An apparatus according to claim 11, wherein said measuring window is sealingly closed by a transparent plate.

13. An apparatus for measuring amylose and/or amylopectin content in rice, said apparatus comprising:
    a cabinet;
    a hopper mounted to said cabinet for receiving rice;
    grinding means mounted within said cabinet for grinding the rice from said hopper;
    screening means mounted within said cabinet for screening the rice ground by said grinding means, to feed sample rice to be measured having a particle size smaller than a predetermined value, to a predetermined filling position;
    a sample container for containing said sample rice;
    a holder for detachably holding said sample container;
    transport means for transporting said holder between said filling position and a measuring position remote therefrom;
    a near infrared spectrometer including a light source for applying light to said sample rice within said sample container held by said holder located at said measuring position, optical means located between said light source and said sample rice for permitting passage of near infrared light beam having its wavelength within a range of from about 1900 nm to about 2500 nm, of the light from said light source, and luminous intensity detecting means for detecting luminous intensity of the light reflected from and/or transmitted through said sample rice to generate signals representative of the luminous intensity;
    control means including memory means for storing therein content conversion coefficients set for the amylose and/or amylopectin, and calculation means for calculating the amylose and/or amylopectin content in said sample rice, based on the content conversion coefficients and said signals from said luminous intensity detecting means; and display means connected to said control means for displaying the amylose and/or amylopectin content calculated by said calculation means.

14. An apparatus according to claim 13, including: turning means for turning said holder located at said filling position between a first position permitting said sample container held by said holder to receive the sample rice fed from said screening means and a second position permitting the sample rice to freely fall from said sample container.

15. An apparatus according to claim 14, wherein said near infrared spectrometer comprises an integrating sphere including a light intake window through which the light from said light source passes, a measuring window which is provided at a location diametrically opposite to said light intake window and which opens at said predetermined measuring position, and a transparent plate sealingly closing said measuring window.

16. An apparatus according to claim 15, wherein said sample container has a transparent bottom wall, and said detecting means includes a luminous intensity detecting element located at said measuring position, said sample container held by said holder being located between said transparent plate and said luminous intensity detecting element when said holder occupies said measuring position.

17. An apparatus according to claim 16, wherein said detecting means further includes at least one luminous intensity detecting element arranged within said integrating sphere.

18. An apparatus according to claim 16, including:
first and second cleaning means connected to said holder, said first and second cleaning means moving together with said holder when the latter is moved by said transport means between said filling position and said measuring position, to clean respectively said transparent plate and said luminous intensity detecting element.

* * * * *

UNITED STATES PATENT AND TRADEMARK OFFICE
CERTIFICATE OF CORRECTION

PATENT NO. : 4,800,280
DATED : January 24, 1989
INVENTOR(S) : Toshihiko SATAKE

It is certified that error appears in the above-identified patent and that said Letters Patent is hereby corrected as shown below:

Column 18, claim 13, line 60, delete "about".

Column 18, claim 13, line 61, delete "about".

Signed and Sealed this

First Day of August, 1989

*Attest:*

DONALD J. QUIGG

*Attesting Officer*      *Commissioner of Patents and Trademarks*